(12) United States Patent
Rönnholm et al.

(10) Patent No.: US 9,975,658 B2
(45) Date of Patent: May 22, 2018

(54) DISPOSABLE CONTAINER AND MIXING SYSTEM COMPRISING THE CONTAINER

(71) Applicant: GE Healthcare Bio-Sciences AB, Uppsala (SE)

(72) Inventors: David Rönnholm, Uppsala (SE); Klaus Gebauer, Uppsala (SE); Rolf Hjorth, Uppsala (SE); Patrick Jonsson, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 302 days.

(21) Appl. No.: 14/895,984

(22) PCT Filed: Jun. 2, 2014

(86) PCT No.: PCT/SE2014/050667
§ 371 (c)(1),
(2) Date: Dec. 4, 2015

(87) PCT Pub. No.: WO2014/196915
PCT Pub. Date: Dec. 11, 2014

(65) Prior Publication Data
US 2016/0114935 A1    Apr. 28, 2016

(30) Foreign Application Priority Data
Jun. 5, 2013  (SE) ...................... 1350689

(51) Int. Cl.
*B01F 7/16* (2006.01)
*B65D 8/02* (2006.01)
(Continued)

(52) U.S. Cl.
CPC .......... *B65D 11/08* (2013.01); *B01F 7/00225* (2013.01); *B01F 7/162* (2013.01);
(Continued)

(58) Field of Classification Search
CPC ....................................................... B01F 7/162
(Continued)

(56) References Cited

U.S. PATENT DOCUMENTS

| 90,594 | A | * | 5/1869 | Sissons | .................. | A47J 43/046 |
|---|---|---|---|---|---|---|
| | | | | | | 366/205 |
| 2,432,291 | A | * | 12/1947 | Dayton | ................... | A47L 15/06 |
| | | | | | | 134/114 |

(Continued)

FOREIGN PATENT DOCUMENTS

| CN | 1468188 A | 1/2004 |
|---|---|---|
| CN | 101035745 A | 9/2007 |

(Continued)

OTHER PUBLICATIONS

Ling et al., "Design Manual for Non-Standard Devices", National Defense Industry Press, Book—4, Dec. 31, 1983, pp. 354.

(Continued)

*Primary Examiner* — David Sorkin
(74) *Attorney, Agent, or Firm* — Wood IP LLC (57) ABSTRACT

A disposable container comprising a side wall, top and bottom, wherein the side wall comprises a first flexible material and the bottom comprises a rigid or semi-rigid material. The side wall top and bottom are joined together to define the container with an interior compartment for keeping a fluid inside the container. The bottom comprises at least one opening that is fluid-tightly covered with an assembly comprising a second flexible material. The assembly comprises at least one port which provides access to the interior compartment of the container. The invention also relates to a mixing system comprising the disposable container.

12 Claims, 10 Drawing Sheets

(51) Int. Cl.
*C12M 1/00* (2006.01)
*C12M 1/06* (2006.01)
*B01F 7/22* (2006.01)
*B65D 6/00* (2006.01)
*B65D 25/24* (2006.01)
*B01F 15/00* (2006.01)
*B01F 7/00* (2006.01)
*B01F 13/00* (2006.01)
*B01F 13/08* (2006.01)

(52) U.S. Cl.
CPC .............. *B01F 7/22* (2013.01); *B01F 13/004* (2013.01); *B01F 13/0872* (2013.01); *B01F 15/0085* (2013.01); *B01F 15/00772* (2013.01); *B65D 11/20* (2013.01); *B65D 25/24* (2013.01); *C12M 23/02* (2013.01); *C12M 23/26* (2013.01); *C12M 23/28* (2013.01); *C12M 27/02* (2013.01)

(58) Field of Classification Search
USPC ................................ 366/205, 314; 383/121.1
See application file for complete search history.

(56) References Cited

U.S. PATENT DOCUMENTS

| | | | |
|---|---|---|---|
| 2,688,473 A * | 9/1954 | Posch | B28C 5/1223 192/48.92 |
| 3,713,839 A | 1/1973 | Delente et al. | |
| 3,962,892 A * | 6/1976 | Garlinghouse | B01F 11/0045 134/118 |
| 5,538,342 A | 7/1996 | Aoshima | |
| 6,375,040 B1 | 4/2002 | Allanson et al. | |
| 6,432,698 B1 | 8/2002 | Gaugler et al. | |
| 7,524,111 B1 * | 4/2009 | Williams | B65D 31/06 220/23.87 |
| 2004/0027912 A1 * | 2/2004 | Bibbo | A61L 2/02 366/149 |
| 2004/0114457 A1 * | 6/2004 | McGill | A47J 36/022 366/199 |
| 2005/0002274 A1 * | 1/2005 | Terentiev | B01F 1/0011 366/273 |
| 2005/0126997 A1 | 6/2005 | Langhans et al. | |
| 2006/0078987 A1 | 4/2006 | Krier | |
| 2007/0253287 A1 | 11/2007 | Myhrberg | |
| 2011/0151551 A1 | 6/2011 | Yi et al. | |
| 2012/0284991 A1 | 11/2012 | Kusz | |
| 2015/0086138 A1 * | 3/2015 | Murray | B65D 33/02 383/120 |
| 2016/0015217 A1 * | 1/2016 | Rojas Restrepo | A47J 43/046 366/314 |

FOREIGN PATENT DOCUMENTS

| | | |
|---|---|---|
| CN | 101108330 A | 1/2008 |
| CN | 102517200 A | 6/2012 |
| CN | 102725201 A | 10/2012 |
| EP | 1842800 A2 | 10/2007 |
| EP | 2141224 A1 | 1/2010 |
| EP | 2509882 A2 | 10/2012 |
| EP | 3004319 A1 | 4/2016 |
| JP | 03029139 U1 | 3/1991 |
| JP | 03123525 U1 | 12/1991 |
| JP | 08192038 A | 7/1996 |
| JP | 2007276881 A | 10/2007 |
| WO | 2005118771 A2 | 12/2005 |
| WO | 2008106193 A1 | 9/2008 |
| WO | 2011071897 A2 | 6/2011 |
| WO | 2011090781 A1 | 7/2011 |
| WO | 2013040161 A1 | 3/2013 |
| WO | 2014/196915 A1 | 12/2014 |

OTHER PUBLICATIONS

Lu et al., "Structural Design of Composite Material", East China Chemical Industry College Press, Apr. 30, 1991, pp. 173.
International Preliminary Report on Patentability Received for PCT Patent Application No. PCT/SE2014/050667, dated Dec. 17, 2015, 8 Pages.
Office Action Received for Chinese Patent Application No. 201480032362.7, dated Jul. 13, 2017, 13 pages (English Translation Only).
Unofficial English translation of Office Action issued in connection with corresponding SE Application No. 1350689-4 dated Dec. 18, 2013.
International Search Report and Written Opinion issued in connection with corresponding PCT Application No. PCT/SE2014/050667 dated Sep. 16, 2014.
Chinese Search Report from CN Appl. No. 201480032362.7, dated Nov. 28, 2016.
Supplementary European Search Report from EP Appl. No. 14 80 7725, dated Dec. 22, 2016.
Japan Notice of Preliminary Rejection for Japanese Patent Application No. 2016-518301, dated Mar. 13, 2018, 3 pages.

* cited by examiner

DISPOSABLE CONTAINER AND MIXING SYSTEM COMPRISING THE CONTAINER

TECHNICAL FIELD

Embodiments of the present invention relate to a technical field of disposable containers and mixing systems comprising disposable containers.

BACKGROUND

Single-use or disposable systems are rapidly increasing in different industries and especially in industries that require use of clean rooms, such as in biopharmaceutical industry. Disposable systems are flexible and cost-effective and for example cleaning processes may be reduced. Disposable components in disposable systems are sterilized and it is assured that they are qualified to regulatory requirements. Disposable systems are easy to adapt to different production purposes and it is easy and less costly than traditionally to change a product line while good process reliability may be maintained or even improved.

There are several kinds of disposable systems, such as mixing systems, in which disposable containers or bags are used. These containers or bags comprise often sheets of flexible material, such as plastic, plastic laminates or corresponding materials.

One type of mixing system in which such containers can be used is a bioreactor system in which cells or microorganisms can grow. Mixing systems include also systems used to prepare for example buffer and media.

Mixing systems may comprise a support or vessel which supports or houses a disposable bag or container of the above-mentioned type. The support may be a support plate or tray for a bioreactor bag of a kind used in GE Healthcare WAVE Bioreactor®. The vessel may be a tank-type support which has a substantially cylindrical form, for example substantially circular cylindrical and is made of rigid material such as stainless steel to provide sufficient support for the flexible bag or container, for example of a kind used in Xcellerex XDR™ Single-use bioreactors. The flexible container or bag is placed inside the vessel in an accurate manner so that for example different pipelines or tubes, mixers and sensors can be connected to the bag properly and accurately. WO 2005/118771 A2 discloses a disposable system of this kind.

Containers may vary in size from about 1-2000 liters. To stabilize or reinforce the containers or to enable the connection of different pipelines or sensors to the containers they often comprise portions of rigid or semi-rigid materials. These rigid or semi-rigid portions provide a platform for safe and secure attachment of for example sensors, pipelines for fluids (both gas and liquid) and mixers. Further, the rigid or semi-rigid parts can reinforce and stabilize the containers and therefore facilitate placing of the containers into mixing vessels in accurate manner.

The materials used in the disposable containers are thermoplastic and the containers may be produced for example by moulding technologies. However, the moulding tools are expensive and complicated to manufacture and thus if there is a need to modify the form or functionality of the container, it may be complicated or costly. Therefore, there is a need for containers and mixing systems that are easy to adapt to changing process needs.

SUMMARY OF THE INVENTION

The object of embodiments of the present invention is to provide a container and a mixing system that are easy to adapt to different process and customer needs.

In an embodiment, a disposable container comprises a side wall, top and bottom, wherein the side wall comprises a first flexible material and the bottom comprises a rigid or semi-rigid material, wherein the side wall, top and bottom are joined together to define the container with an interior compartment for keeping a fluid inside the container. The bottom comprises at least one opening that is fluid-tightly covered with an assembly comprising a second flexible material and wherein the assembly comprises at least one port which provides access to the interior compartment of the container. The assembly is manufactured separately from the rigid or semi-rigid bottom and it is easy to adapt the amount of openings and ports in the assembly according to the customer and/or process needs. Thus an easy way to adapt the container to different needs is provided.

The rigid or semi-rigid bottom may comprise a rim that extends vertically towards the interior compartment of the container to facilitate the joining of the side wall and the bottom.

The container has a vertical central axis and a horizontal axis perpendicular to the vertical axis. According to one aspect of the invention, the bottom of the container is circular and comprises a first half (I) and a second half (II) divided by the diameter of the circular bottom. The bottom is inclined in relation to the horizontal axis such that the first half (I) of the bottom is inclined towards the centre of the interior compartment of the container and the second half (II) of the bottom is inclined outwards of the centre of the interior compartment of the container. In this manner, a structure facilitating for example drainage of the container may be provided. Also it is possible to place sensors, spargers and mixing equipment in different levels and thus improve for example mixing or gas supply to the container. The angle of inclination may be for example from 1° to 45°, such as between 1° to 25°.

The inclined bottom may comprise draining means in the second half of the bottom. Since the second half is inclined outwards of the centre of the interior compartment the lowest point in relation to the vertical axis (V) is located in the second half, and thus gravity can be utilized in draining of the container, and therefore, efficient draining of the container can be provided.

The bottom may comprise a mixing impeller means on the first half of the bottom having the highest point in respect to the vertical axis. In this way, asymmetric placement both in vertical and horizontal direction can be provided. This has surprisingly improved the mixing operation. One advantage has been that solid or semi-solid materials do not accumulate around the impeller due to its position on the first half having a higher vertical position than for example draining means. Thereby, the solids or semi-solids flow towards the draining means instead of accumulating around the impeller.

The top of the container may comprise a rigid or semi-rigid material. This further improves the stability of the container. The top may also comprise at least one opening that is fluid-tightly covered with the assembly comprising a second flexible material and wherein the assembly comprises at least one port which provides access to the interior compartment of the container. In this way, tubes and other couplings may be provided both on the bottom and top of the container, whereby the flexibility of the container is further improved.

The first flexible material and the second flexible materials may be the same materials. The materials could also be different depending on for example the size of the container and the requirements for the support the ports in the assembly need. In an embodiment, the first flexible material and/or the second flexible material is a plastic laminate. In an embodiment, the flexible materials are also thermoplastic, and therefore the side wall, top and bottom can be joined together by means of a heat seal. Additionally or alternatively, they may be joined together by means of an adhesive seal.

The bottom may comprise at least two openings fluid-tightly covered with the assembly. This enables the use of several connections and couplings and it also enables adjustable positioning of these connections or couplings in relation to each other.

In an embodiment, the bottom is circular and has a radius (r), and the bottom comprises an opening in the centre of the bottom having a radius that is larger than 0.5(r). In this way the rigid or semi-rigid material of the bottom provides a rim-shaped bottom around the circumference of the bottom, whereby the need for rigid or semi-rigid material may be reduced and thus a lighter and more economic structure obtained.

Embodiments of the present invention further relates to a mixing system comprising a vessel for housing the above described disposable container. The vessel may be made of a rigid and dimensionally stable material, such as stainless steel. The vessel comprises a base supporting the disposable container and a sidewall extending vertically upwards from the base. The base is provided with at least one opening to be in association with the assembly, which assembly comprises at least one port that provides access to the interior compartment of the container. Thus, the mixing system is flexible and an easy way to adapt the system to different needs is provided.

The base of the vessel may be inclined in a corresponding angle as the bottom of the container. In this way, sufficient support for the container may be provided without the need for additional supporting arrangements. The base may be horizontal and thus not inclined. In this case additional supporting element may be needed, especially if the bottom of the container is inclined.

The mixing system may comprise a frame, and the base may be releasably attached to the frame. In this way, it is possible to change the base so that it conforms to the bottom of the container. For example, the system may be provided with an inclined base and a non-inclined base, and the base is simply changed depending on the container used and thus no additional supporting structures are needed.

The base may also comprise a plurality of openings. For example it may be prepared to match all possible openings that could be in association with the assembly comprising ports. The openings that are not needed in the system may be then covered by covering caps that are detachably attached to the opening. This provides a smooth surface for the base that lies against the disposable container and thus provides improved mechanical support for the container. Since the caps are detachably attached to the openings, the flexibility of the system is maintained.

BRIEF DESCRIPTION OF THE DRAWINGS

Embodiments of the present invention will be discussed in detail below with reference to the attached drawings. The embodiments shown in the figures are examples and should not be regarded as limiting the present invention in any way.

DETAILED DESCRIPTION

In FIGS. 1-8 examples of containers and systems according to embodiments of the present invention are shown. The skilled person realizes however that for example the container 1 shown in FIG. 1 may have another form or be of another type as long as the container comprises a side wall, top and bottom, wherein the side wall comprises a first flexible material and the bottom comprises a rigid or semi-rigid material and wherein the side wall, top and bottom are joined together to define the container with an interior compartment for keeping a fluid inside the container. The fluid can be liquid and/or gas. The container may have a volume of from about 10 to 5000 liters, such as from 10 to 2000 liters.

What is meant by flexible material, both the first and the second flexible material used in an embodiment of the present invention, is a material that can be easily bent without breaking. The flexible material may have a thickness of less than 1 mm, suitably from about 0.005 mm to about 0.7 mm, and more particularly from about 0.01-0.5 mm depending on the size and form of the container or bag. The flexible material may have a flexural modulus according to ASTM D790 of less than 2000 MPa. The flexibility of the material is further defined by the thickness of the material, i.e., basically that the thinner the material the more flexible the material. However, two materials of equal thickness may have different flexibility due to the differences in flexural modulus of the materials.

Both the first and the second flexible materials may be a polymeric film material and can be made of a mono layer material or a laminate comprising two or more layers, e.g., polymeric material films. The thickness of one or both of the polymer film materials may, e.g., be 50-400 micrometers, such as 100-300 micrometers. The flexible material comprises at least one layer of a polymeric film material having thermoplastic properties. In an embodiment, the polymeric film material may be sterilizable and more particularly resists gamma radiation, i.e., it substantially retains its properties after gamma radiation. Suitable materials may be conventional film materials used in packaging industry and for example mono layer or multi-layer PE (polyethylene), ULDPE (Ultra Low Density Polyethylene), LLDPE (Linear Low density Polyethylene), EVOH (Ethylene Vinyl Alcohol) and PA (polyamide). The material may also be a laminate film comprising one or more polymeric materials or the material may be for example multi-layer coextruded polyethylene film, such as ULDPE/EVOH/PE/PA. The laminate film may be further comprised of two or more material layers of different thermoplastic materials which have different melting points. However, the mentioned flexible materials are only examples of suitable materials and any flexible material with thermoplastic properties which fulfills product requirements can be used. The first and the second flexible materials may be the same or different from each other, depending on the product requirements.

By rigid or semi-rigid material is meant a material which is unbending or may be slightly bent, i.e., it has slightly flexible and/or elastic properties. In an embodiment, the flexural modulus of the rigid material is greater than 200 MPa according to ASTM D790. The flexural modulus value may be overlapping with the flexural modulus value of the flexible material, but the rigidity of the material is further defined by the thickness of the material. The rigid material can have a thickness of from about 0.7 mm. There is no upper limit for the thickness of the rigid material. The rigid or semi rigid material is further substantially dimensionally stable and is more particularly moldable and can be a polymeric material. Examples of suitable materials are for example low density polyethylene or high density polyethylene materials, polyamide or polypropylene. Further, the rigid or semi rigid material may be a composite material comprising a polymer matrix, such as a polyester, vinyl ester, polyamide polypropylene or any other mouldable polymer material. In an embodiment, the polymer material has thermoplastic properties and can be sterilized and more particularly resists gamma radiation, i.e., it substantially retains its properties after gamma radiation. The rigid parts can be for example vacuum formed or moulded for example by injection moulding.

The seal between the flexible and the rigid or semi-rigid material, i.e., between the top, bottom, side wall and the assembly of an embodiment of the present invention, can be obtained by several means. The seal should be fluid-tight so that sterile conditions inside the container can be maintained. The seal can be obtained by means of an adhesive, by heat-sealing or by using both heat-sealing and adhesive.

In an embodiment, the adhesives used in the adhesive seal are medical grade adhesives. The adhesives can be for example hot-melt adhesives, UV-curable adhesives or solvent-based adhesives. In an embodiment, the hot-melt adhesives used may have a lower melting point than the flexible film material so that the flexible film does not melt when the hot-melt adhesive is applied to the material. Examples of adhesives are for example epoxy- or silicone-based adhesives, such as MasterBond X17 and 3M DP8005. Further, for example adhesive tape could be used.

The heat seal is obtained by bringing the flexible material in contact with heat, so that the thermoplastic component in the material melts and provides the heat seal. The heat seal may be obtained by any suitable manner, which are per se known to the skilled person, for example by hot air welding or conventional heat mold sealing.

Embodiments of the present invention is further illustrated in the figures as described below.

Figure 1:
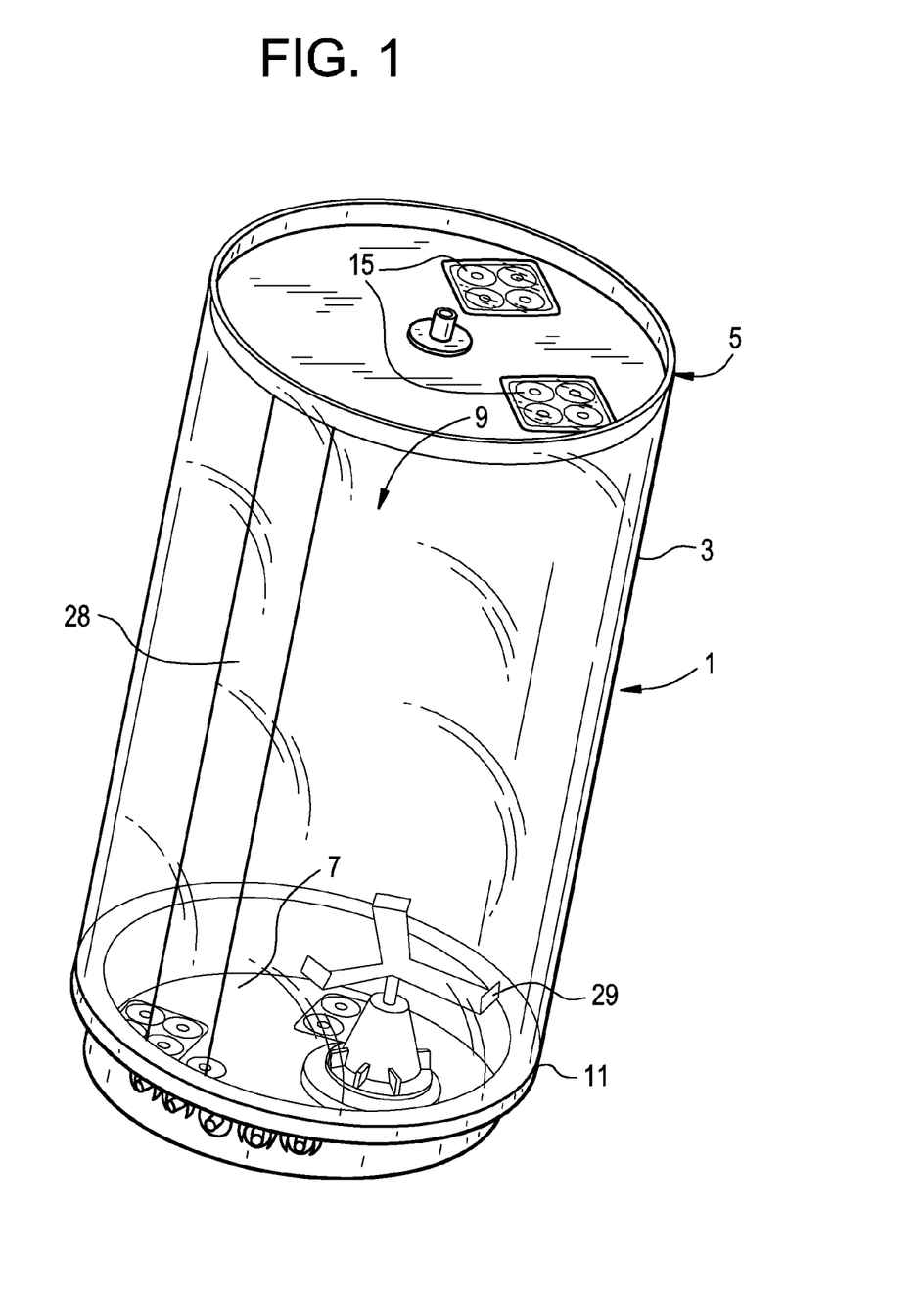
FIG. 1 schematically shows a perspective view of a disposable container according to one embodiment of the invention.

FIG. 1 shows a disposable container 1 comprising a side wall 3 comprising a first flexible material, e.g., a plastic film, and a bottom 7 comprising a rigid or a semi-rigid material. The bottom part 7 of the container 1 stabilizes and reinforces the container 1. The rigid or semi-rigid bottom 7 comprises a rim 11 that extends vertically towards the interior compartment 9 of the container 1 to facilitate the joining of the side wall 3 and the bottom 7. At least one impeller means 29 is provided on the bottom 7, and at least one baffle 28 that extends over the entire height of the container is provided to improve the mixing operation inside the container. The container further comprises a top 5, which is also made of a rigid or semi-rigid material. The top 5 comprises two assemblies 15, provided to cover openings in the top. The assemblies 15 are described more in detail later in the description.

Figure 2A:
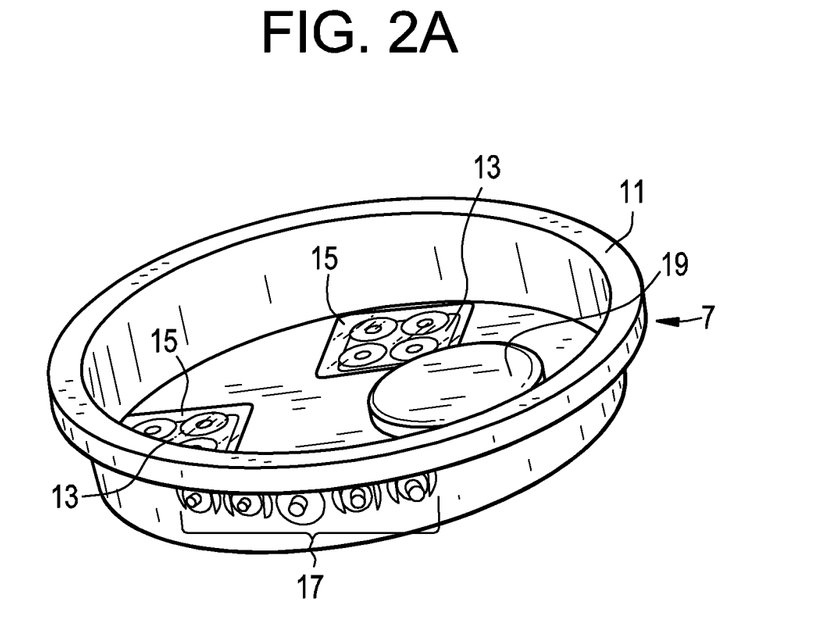
FIGS. 2A, 2B and 2C schematically shows different views and a cross section (FIG. 2B) of a bottom of the container according to one embodiment.

As further illustrated more in detail in FIG. 2A, the bottom 7 comprises a rim 11 that extends vertically upwards. The rim comprises ports 17 for connection of different probes and tubes. Further an impeller base 19 is provided and asymmetrically positioned on or at the bottom 7. The bottom 7 further comprises two openings 13 that are fluid-tightly covered with an assembly 15 comprising a second flexible material, which may be a plastic material as defined above. Each assembly 15 comprises four ports (25, shown more in detail in FIG. 3) that provide access to the interior compartment of the container.

Generally, the ports in the assembly 15 and in the rim 11 provide a connection point to different pipes or tubes and/or sensors through which gases and liquids may be provided in or harvested or drained from the container. These ports may function as sterile connections and for example enable sample taking from the container. It is also possible to connect different sensors to the ports whereby it is easy to observe the conditions in the container. The amount of the ports may be easily adjusted by means of the assembly according to the needs in the container or system. The assembly may be provided with several ports or it may only contain one port. Since the ports are provided on a flexible material, the amount of the ports may be easily adjusted. The assembly may be manufactured separately from the rigid or semi-rigid bottom and the amount of openings and ports in the assembly can be adapted to the customer and/or process needs. Thus an easy way to adapt the container to different needs is provided.

It is also possible to have one or more flexible sensor patches, comprising one or more sensors in a patch of flexible material attached to the side wall of the bioreactor. If the sensors are essentially flat, they will not disturb the alignment of the side wall with the support vessel.

Figure 3:
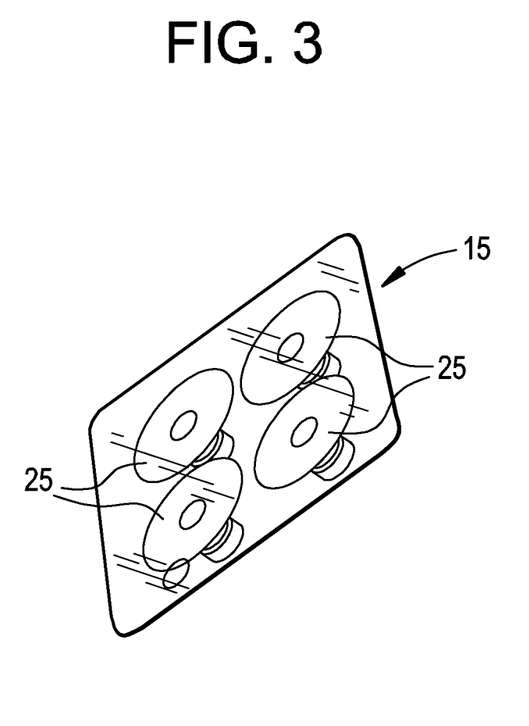
FIG. 3 shows a view of an assembly comprising ports.

An example of an assembly 15 with four ports 25 is shown in FIG. 3.

Figure 2B:
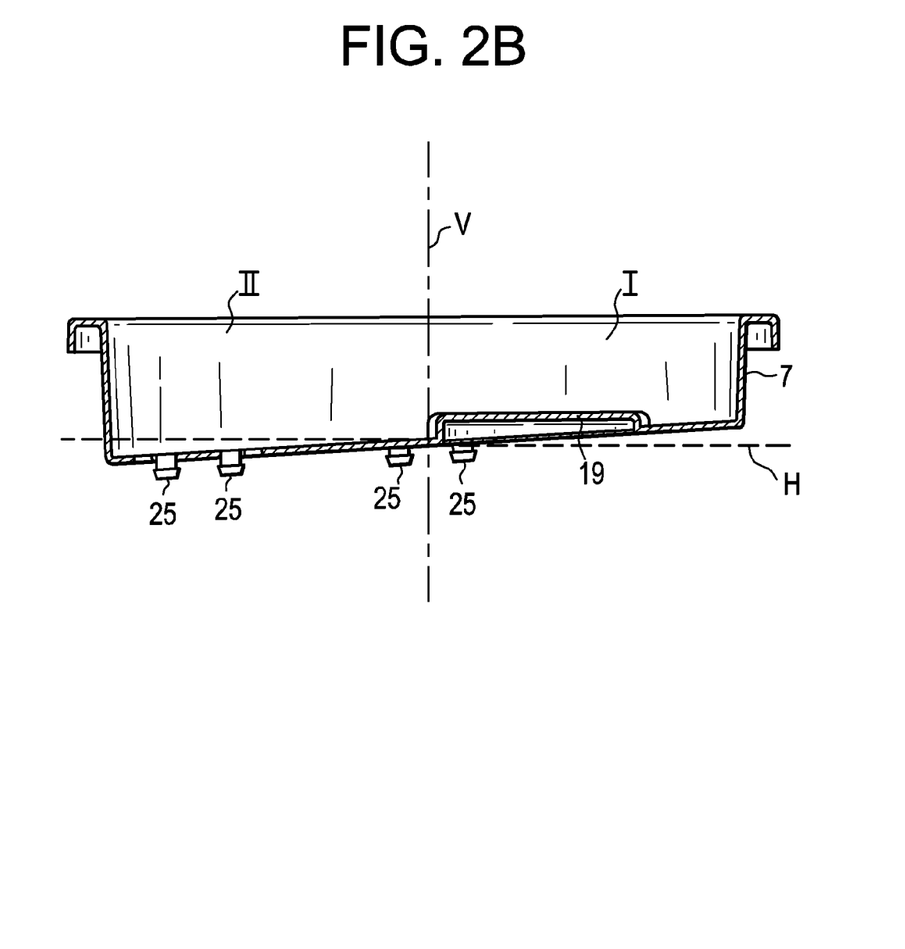

FIG. 2B shows a cross section of the bottom 7. The container has a vertical central axis (V) and a horizontal axis (H) perpendicular to the vertical axis (V), as illustrated in FIG. 2B. FIGS. 1 and 2A show that the bottom 7 is circular and comprises a first half (I) and a second half (II) divided by the diameter of the circular bottom 7. The bottom 7 is inclined in relation to the horizontal axis such that the first half (I) of the bottom is inclined towards the centre of the interior compartment of the container and the second half (II) of the bottom is inclined outwards of the centre of the interior compartment of the container 1. The angle of inclination may be for example from 1° to 45°, such as from 1° to 20°.

The inclined bottom may comprise draining means in the second half of the bottom. The draining means may be connected to the ports 25 in the second half (II), or it may be assembled directly in association with the rigid or semi-rigid bottom 7. Since the second half (II) is inclined outwards of the centre of the interior compartment the lowest point in relation to the vertical axis (V) is located in the second half (II), and thus gravity can be utilized in draining of the container. Therefore, efficient draining of the container can be provided.

In another embodiment, only the second half (II) of the bottom, i.e., the half that does not contain the impeller means, is inclined in relation to the horizontal axis (H) outwards of the centre of the interior compartment of the container 1. The first half could be positioned in a horizontal direction in alignment with the horizontal axis (H). Thus, improved stability for the mixer can be provided. Also in this embodiment, the inclined bottom may comprise draining means in the second half of the bottom. The draining means may be connected to the ports 25 in the second half (II), or it may be assembled directly in association with the rigid or semi-rigid bottom 7. Since the second half (II) is inclined outwards of the centre of the interior compartment the lowest point in relation to the vertical axis (V) is located in the second half (II), and thus gravity can be utilized in draining of the container. Therefore, efficient draining of the container can be provided.

In a further embodiment, the draining means could be located substantially in the centre of the bottom. In this embodiment, the bottom could be inclined such that the centre of the bottom containing the draining means is located in the central point of the bottom and this point is arranged as the lowest point. In this embodiment, the bottom forms a slightly funnel-shaped structure, and provides for an even draining of the container.

As shown in FIG. 2B, the bottom 7 comprises an impeller base 19 on the first half of the bottom having the highest point in respect of the vertical axis. In this way, asymmetric placement both in vertical and horizontal direction can be provided, and it has been surprisingly noted that the mixing operation has been improved. Liquids contained in the interior containment may include solid or semi-solid materials. As can be understood from FIG. 2B, the solid or semi-solid materials will not accumulate around the impeller due to its position on the first half but instead flow towards the draining means in the second half (II) of the bottom 7.

Figure 2C:
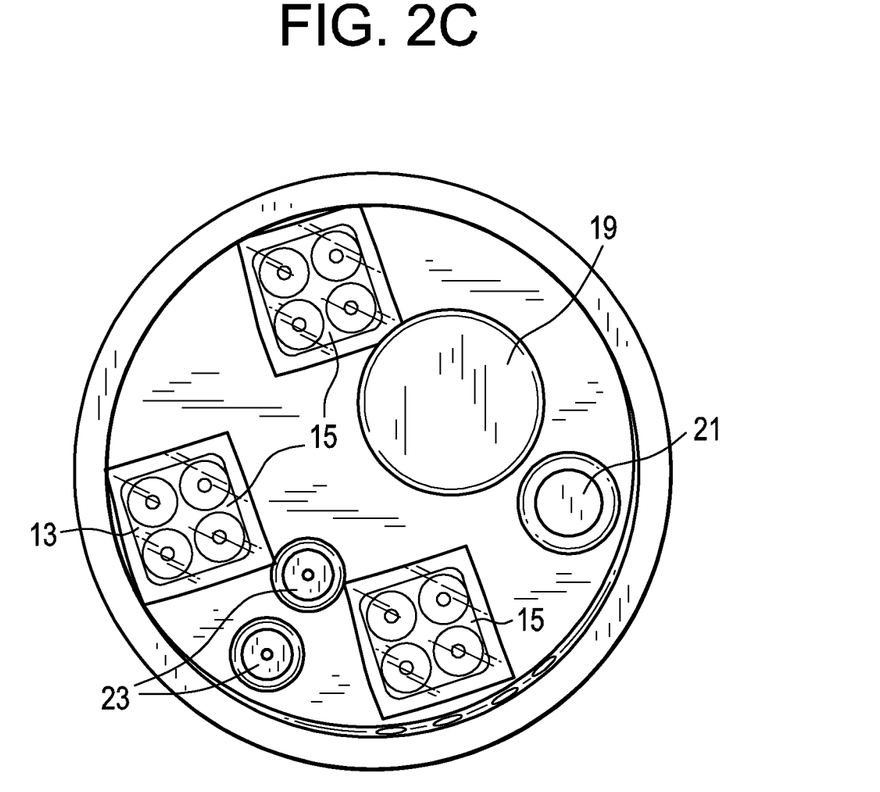

FIG. 2C illustrates an embodiment of the bottom in which three assemblies 15 are sealed or attached to the bottom to cover the openings 13. The bottom further comprises a separate sparger coupling 21 and baffle couplings 23. These couplings 21 and 23 could be provided by the ports 25 of an assembly 15.

Figure 4:
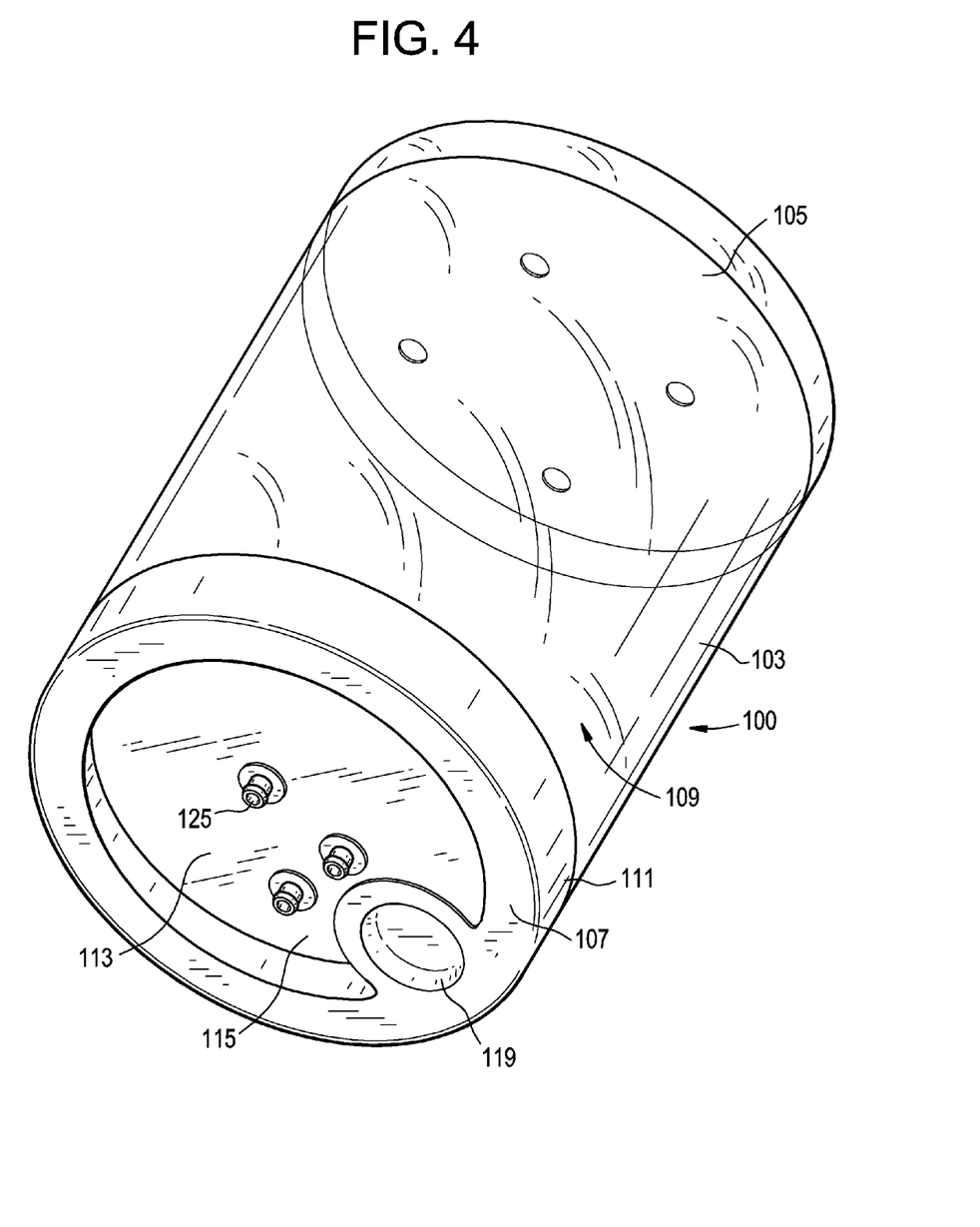
FIG. 4 schematically shows a view from below of another embodiment of a container according to the present invention.

In FIG. 4, another embodiment of the container according to the present invention is illustrated. The container 100 comprises a circular cylindrical side wall 103 and a top 105 of flexible material. As can be seen, the bottom 107 comprises only one large opening 113, whereby only a thin rim extending over the edge area radially towards the centre of the bottom and being integrated with a rim 111 extending vertically towards the interior compartment 109 between the bottom 107 and the side wall 105, is formed of the rigid or semi-rigid material. However, to provide sufficient stability for an impeller means, an impeller base 119 is provided integrated with the rim area. In this embodiment, the assembly 115 provided with ports 125 is larger than the assemblies illustrated in for example FIGS. 2A and 2C.

Figure 5:
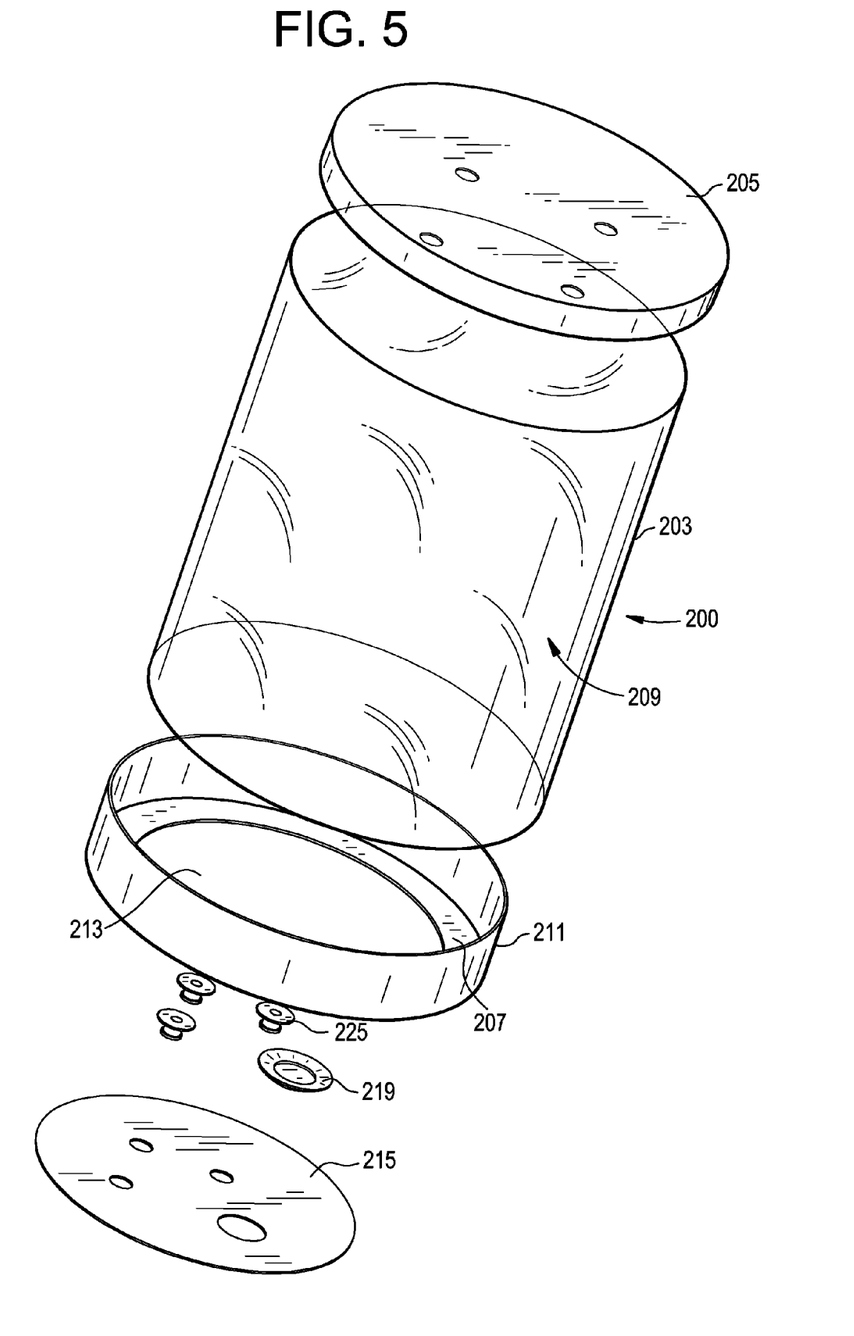
FIG. 5 shows an exploded view drawing of a further embodiment of a container according to the present invention.

The container 200 illustrated in FIG. 5 has a corresponding structure as the container shown in FIG. 4 and comprises a side wall 203, top 205 and bottom 207, an interior compartment 209 and a vertically extending rim 211. However, in this embodiment, the opening 213 in the bottom is circular and the impeller base 219 is attached fluid-tightly to the assembly 215 that also comprises ports 225.

In the embodiments shown in FIGS. 4 and 5 the rigid or semi-rigid material provides a rim-shaped bottom around the circumference of the bottom, and the need for rigid or semi-rigid material may be reduced and thus a lighter and more economic structure can be obtained.

Figure 6:
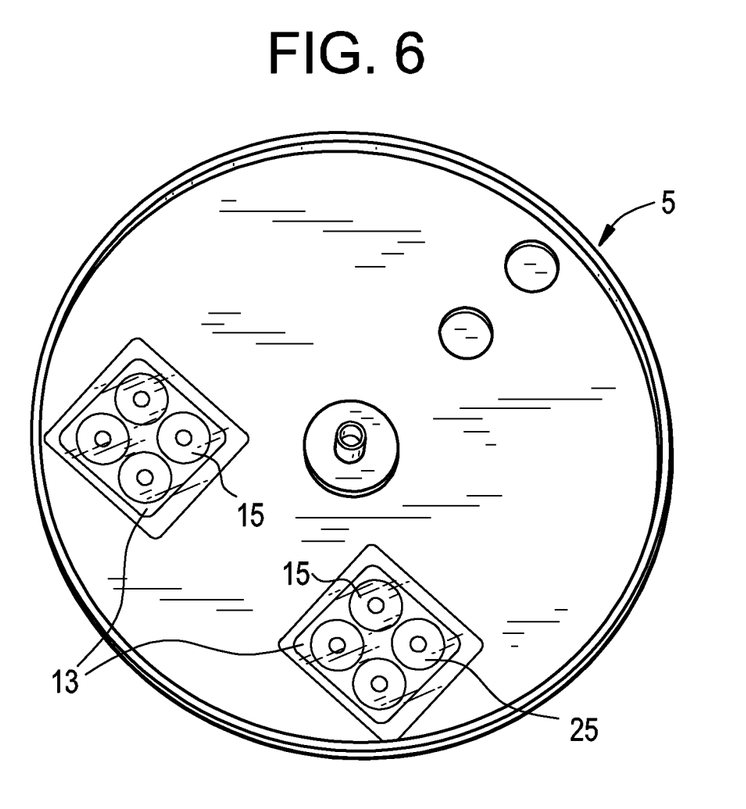
FIG. 6 shows a top view of a top of the container according to one embodiment of the invention.

FIG. 6 illustrates an embodiment of the top 5 according to the present invention. In a similar manner as the bottom 7, also the top 5 may be provided with openings 13 and assemblies 15 comprising the ports 25.

Figure 7:
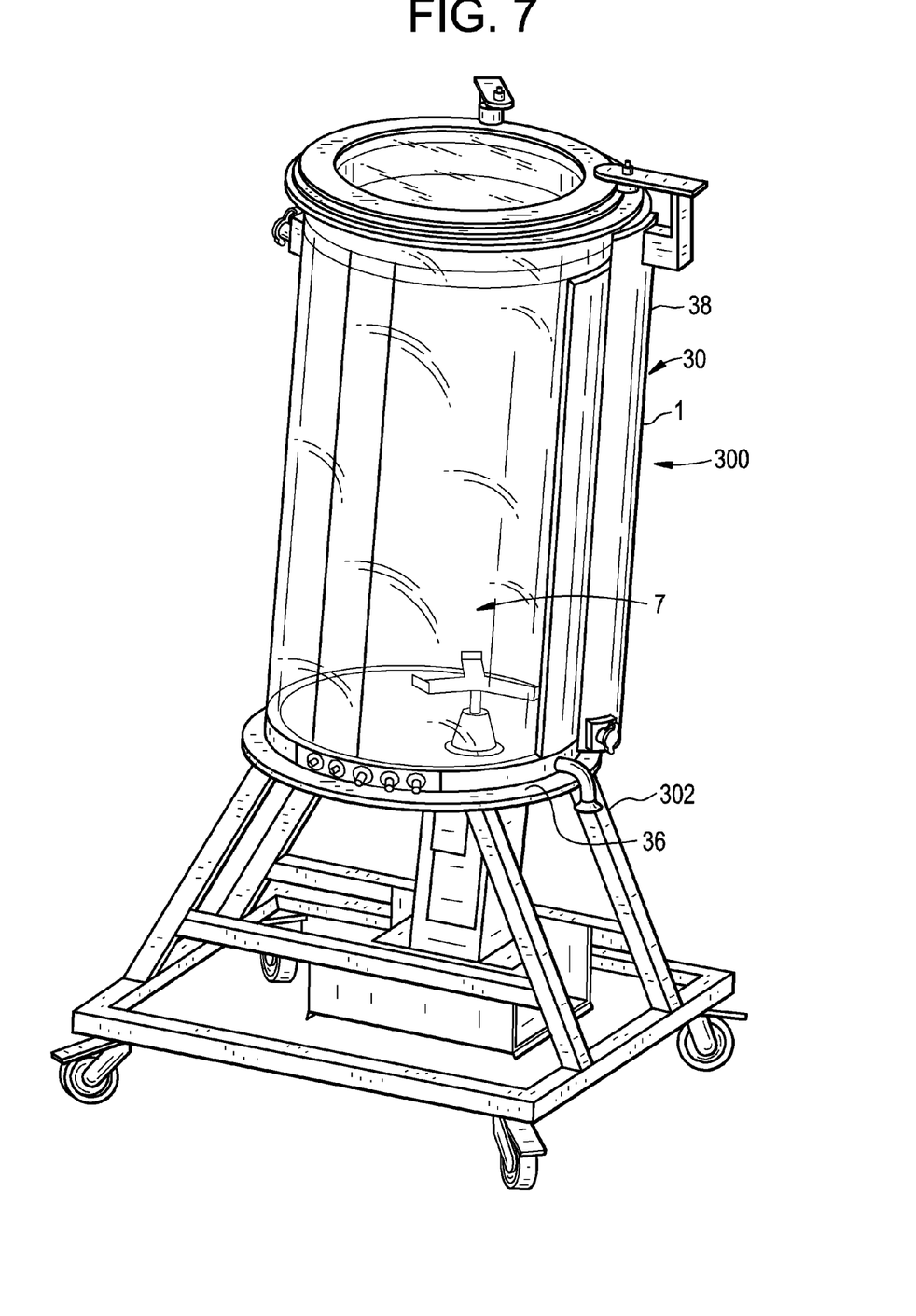
FIG. 7 schematically shows a perspective view of the mixing system including a vessel and the disposable container.
Figure 8:
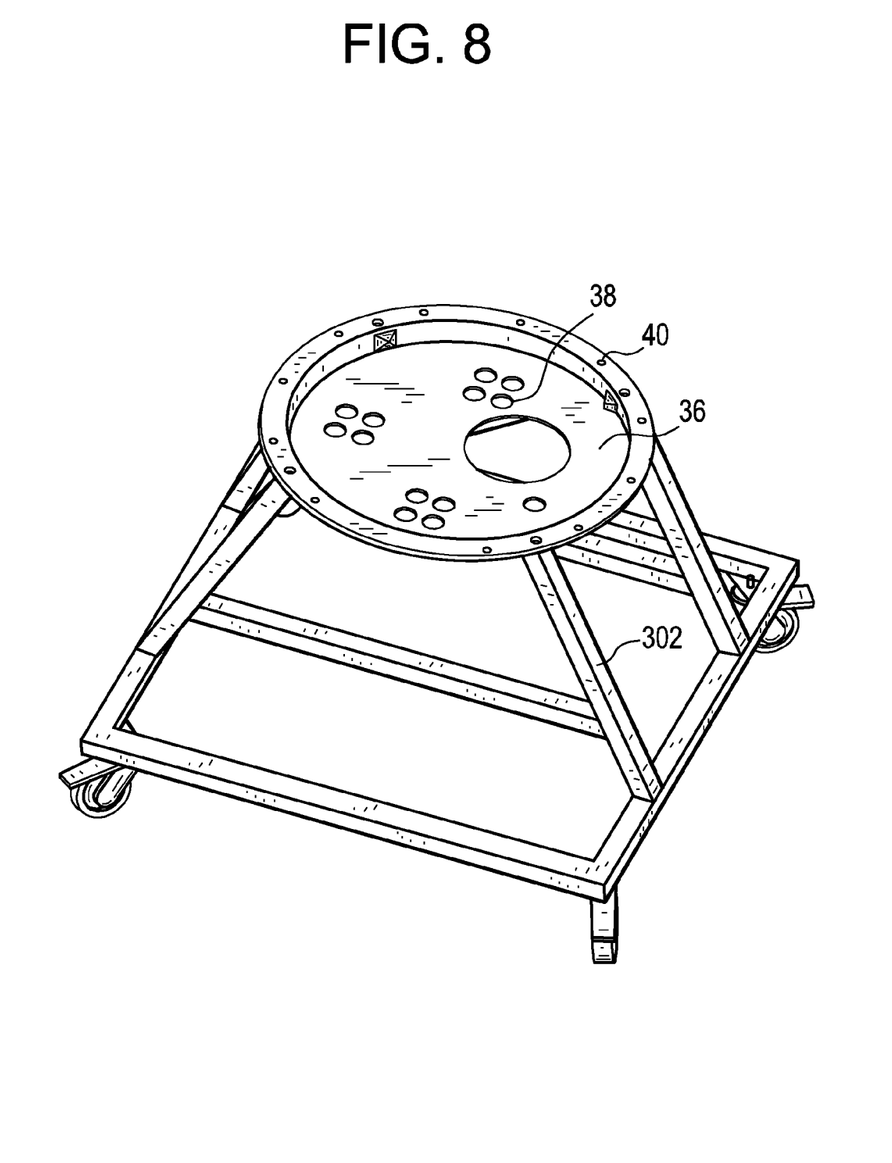
FIG. 8 schematically shows a perspective view of a frame and a base in the mixing system according to an embodiment of the present invention.

Embodiments of the present invention further relate to a mixing system, an example of which is shown in FIG. 7. The mixing system 300 comprises a vessel 30 for housing a disposable container 1. The vessel 30 may be made of a rigid and dimensionally stable material, such as stainless steel. The vessel 30 comprises a base 36 supporting the disposable container 1 and a sidewall 38 extending vertically upwards from the base 36. As illustrated in FIG. 8, the base 36 is provided with several openings 38 that are adapted to be in association with the assembly 15, which comprises the port 25 that provide access to the interior compartment of the container.

As further shown in FIG. 8, the base 36 of the vessel 30 is inclined in a corresponding angle as the bottom 7 of the container 1 making the second half of the base deeper than the first half of the base. Thus, the bottom 7 of the container can be fitted to the base 36 such that the second half (II) of the bottom, that is inclined outwards of the centre of the interior compartment of the container, is fitted in the corresponding deeper half of the base 36 than the other half of the base 36. In this way it can be assured that the container 1 is fitted to the base in a stable manner.

The base is further placed on a frame 302 that supports the mixing system 300. The base 36 is attached to the frame 302 by means of screws, so that it can be easily detached and replaced with another type of base, if needed. Also, it is possible to cover the openings that are not needed with covering caps that are detachably attached to the opening. This provides a smooth surface for the base that lies against the disposable container and thus provides improved mechanical support for the container. Since the caps are detachably attached to the openings, the flexibility of the system is improved while mechanical stability is maintained.

The examples above should not be considered limiting the invention in any way. Instead, the scope of the invention is limited by the appended claims.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A disposable container comprising:
   a side wall, top and bottom, wherein the side wall comprises a first flexible material and the bottom comprises a rigid or semi-rigid material, wherein the side wall, top and bottom are joined together to define the container with an interior compartment for keeping a fluid inside the container, wherein the bottom comprises at least one opening that is fluid-tightly covered with an assembly comprising a second flexible material and wherein the assembly comprises at least one port which provides access to the interior compartment of the container, wherein the container has a vertical central axis and a horizontal axis perpendicular to the vertical axis, wherein the bottom of the container is circular and comprises a first half and a second half divided by the diameter of the circular bottom, wherein the bottom is inclined in relation to the horizontal axis such that the first half of the bottom is inclined towards a centre of the interior compartment of the container and the second half of the bottom is inclined outwards of the centre of the interior compartment of the container.

2. The disposable container according to claim 1, wherein the rigid or semi-rigid bottom comprises a rim that extends vertically towards the interior compartment of the container.

3. The disposable container according to claim 1, wherein the angle of inclination is from 1°-25°.

4. The disposable container according to claim 1, wherein the bottom comprises a drainage structure in the second half of the bottom having the lowest point in relation to the vertical axis.

5. The disposable container according to claim 1, wherein the bottom comprises at least one mixing impeller on the first half of the bottom having the highest point in respect to the vertical axis.

6. The disposable container according to a claim 1, wherein the top comprises a rigid or semi-rigid material.

7. The disposable container according to claim 6, wherein the top comprises at least one opening that is fluid-tightly covered with the assembly comprising a second flexible material and wherein the assembly comprises at least one port which provides access to the interior compartment of the container.

8. The disposable container according to claim 1, wherein the first flexible material and the second flexible material are the same materials.

9. The disposable container according to claim 1, wherein the first flexible material and/or the second flexible material is a plastic laminate.

10. The disposable container according to claim 1, wherein the side wall, top and bottom are joined together by a heat seal and/or an adhesive seal.

11. The disposable container according to claim 1, wherein the bottom comprises at least two openings fluid-tightly covered with the assembly.

12. The disposable container according to claim 1, wherein the bottom is circular and has a radius, and wherein the bottom comprises an opening in the centre of the bottom, wherein the opening has a radius that is larger than one half of the radius of the bottom.

\* \* \* \* \*